(12) United States Patent
Heindl

(10) Patent No.: US 7,795,423 B2
(45) Date of Patent: Sep. 14, 2010

(54) POLYNUCLEOTIDE LABELING REAGENT

(75) Inventor: Dieter Heindl, Paehl (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 317 days.

(21) Appl. No.: 12/123,656

(22) Filed: May 20, 2008

(65) Prior Publication Data
US 2009/0012279 A1 Jan. 8, 2009

Related U.S. Application Data

(63) Continuation of application No. PCT/EP2006/011122, filed on Nov. 21, 2006.

(30) Foreign Application Priority Data

Nov. 23, 2006 (EP) .................................. 05025499

(51) Int. Cl.
*C07H 21/00* (2006.01)
(52) U.S. Cl. ..................... 536/25.3; 536/18.5; 536/18.6; 536/25.31; 536/25.32; 536/25.33
(58) Field of Classification Search .................. None
See application file for complete search history.

(56) References Cited

U.S. PATENT DOCUMENTS 6,313,314 B1 * 11/2001 Cheng et al. ................ 548/549

* cited by examiner

*Primary Examiner*—Patrick T Lewis

(57) ABSTRACT

The present invention provides a new labeling reagent for preparing modified oligonucleotides and processes for their production wherein these oligonucleotides contain at least once the structure P=N—$SO_2$-benzole-L-M-X, characterized in that L is either —$(CH_2)n$- or polyethylene glycol, M is selected from a group consisting of —NH—, —O—, —S—, and —COO—, and X is either a protecting group or a detectable unit. L is preferably either —$(CH_2)n$- or polyethylene glycol.

6 Claims, No Drawings

SEQUENCE LISTING

```
<160> NUMBER OF SEQ ID NOS: 2

<210> SEQ ID NO 1
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)
<223> OTHER INFORMATION: A-N-SO2-Ph-NH-C(=O)-(CH2)5-NH2
<220> FEATURE:
<221> NAME/KEY: modified_base
<222> LOCATION: (36)
<223> OTHER INFORMATION: T-N-SO2-Ph-NH-C(=O)-(CH2)5-NH2

<400> SEQUENCE: 1
agggatctgc tcttacagat tagaagtagt cctatt                           36

<210> SEQ ID NO 2
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)
```

```
<223> OTHER INFORMATION: A-N-SO2-Ph-NH-C(=O)-(CH2)5-NH LC Red 640
<220> FEATURE:
<221> NAME/KEY: modified_base
<222> LOCATION: (36)
<223> OTHER INFORMATION: T-N-SO2-Ph-NH-C(=O)-(CH2)5-NH LC Red 640

<400> SEQUENCE: 2
agggatctgc tcttacagat tagaagtagt cctatt                         36
```

POLYNUCLEOTIDE LABELING REAGENT

RELATED APPLICATIONS

This is a continuation of PCT/EP2006/011122 filed Nov. 21, 2006 and claims priority to EP 05025499.4 filed Nov. 23, 2005.

FIELD OF THE INVENTION

The present invention concerns new substances and processes for producing them in the field of nucleotide chemistry. These substances are so-called phosphate mimetics in which a hydroxyl group is replaced by a corresponding mimetic. In particular the present invention concerns a labeling reagent for preparing a new class of modified oligonucleotides.

BACKGROUND

Various methods are known in the art for the synthesis of nucleotides or oligonucleotides with a modified phosphate moiety. Synthetic (deoxy) oligonucleotides are usually prepared on a solid phase with the aid of phosphoramidite chemistry. Glass beads with pores of a defined size are usually used as the solid phase (abbreviated in the following as CPG= controlled pore glass). The first monomer is linked to the support by a cleavable group so that the free oligonucleotide can be cleaved off after completion of the solid phase synthesis. In addition the first monomer contains a protected hydroxyl group in which case dimethoxytrityl (DMT) is usually used as the protective group. The protective group can be removed by acid treatment. Then at the 5' end 3' phosphoramidite derivatives of (deoxy) ribonucleosides that are also provided with a DMT protective group are successively coupled to the reactive group that is freed in each case of the DMT protective group in a cyclic process. Alternatively 3' dimemoxytrityl-protected 5' phosphoramidites are used in inverse oligonucleotide synthesis. The H-phosphonate strategy is also used in particular to introduce modifications on the phosphate backbone, e.g., to prepare radiolabeled phosphorothioates. Various strategies are also already known for preparing modified or labeled oligonucleotides: trifunctional support materials are used according to the prior art to prepare oligonucleotides labeled at the 3' end (U.S. Pat. Nos. 5,290, 925, 5,401,837). Labeled phosphoramidites in which the labeling group is bound to the phosphoramidite via a C3-12 linker are usually used to prepare oligonucleotides labeled at the 5' end (U.S. Pat. Nos. 4,997,928, 5,231,191). Furthermore modifications can be introduced into oligonucleotides on the individual bases (U.S. Pat. Nos. 5,241,060, 5,260,433, 5,668, 266) or by introducing internal non-nucleoside linkers (U.S. Pat. Nos. 5,656,744, 6,130,323).

Alternatively an internucleoside phosphate can be labeled by postsynthetic labeling of phosphorothioates (Hodges, R. R., et al., Biochemistry 28 (1989) 261-7) or by post-labeling a functionalized phosphoramidite (Agrawal, S., Methods in Mol. Biology 26 (1994) Protocols for Oligonucleotide Conjugates, Chapter 3; Humana Press, Totowa, N.J.). However, these methods have not gained acceptance due to the instability of the phosphoramidites and phosphoric acid thioesters.

It is also already known from the prior art that modifications can be introduced on the inter-nucleoside phosphate residue of oligonucleotides. In the most prominent cases these are phosphothioates (Burgers, P. M., and Eckstein, F., Biochemistry 18, (1979) 592-6), methylphosphonates (Miller, P. S., et al., Biochemistry 18 (1979) 5134-43) or boranophosphates (WO 91/08213). Special monomers have to be synthesized in order to prepare methylphosphonate oligonucleotides. In contrast conventional phosphoramidites or H-phosphonates can be used to synthesize phosphorothioates and boranophosphates in which case the borano or thio modification can be introduced directly during or also after oligonucleotide synthesis by using special reagents that react with the H-phosphonate or with the phosphonic acid triester. Although all these methods lead to modified oligonucleotides, the requirements of the synthesis chemistry used for this does not allow labels that can be detected in this manner or functional groups to be directly introduced on the phosphate backbone of the oligonucleotide chain during oligonucleotide synthesis.

Baschang, G., and Kvita, V., "Angewandte Chemie" 85(1) (1973) 43-44 describe the reaction of a nucleotide phosphoric acid triester with azides such as methylsulfonyl azide to prepare tri-alkyl(aryl)imidophosphates which are, however, unstable and decompose.

Nielsen, J., and Caruthers, M. H., J. Am. Chem. Soc. 110 (1988) 6275-6276 describe the reaction of deoxynucleoside phosphites provided with a 2-cyano-1,1-dimethylethyl protective group in the presence of alkyl azide. Furthermore, the authors suggest that this principle is suitable for preparing nucleotides that are modified on the phosphate residue without elucidating which types of modifications prepared with the aid of the disclosed method could have particular advantages. In particular the authors suggest the introduction of alkyl residues.

WO 89/09221 discloses N-alkyl phosphoramidites or rather oligonucleotides substituted with N-alkyl on at least one phosphate residue which are prepared by oxidizing nucleoside phosphites (provided with a protective group) with iodine in the presence of suitable alkylamines.

WO 03/02587 discloses the preparation of modified oligonucleotides in which H-phosphates are converted by amination into phosphoramidates.

Thus all of these publications describe the preparation of molecules which contain a phosphoramidate instead of a phosphate residue. However, molecules containing phosphoramidate are susceptible to hydrolysis since the amine group is protonated in an acidic environment and is then substituted by water.

In addition WO 01/14401 proposes nucleotide building blocks or oligonucleotides in which a phosphate residue is substituted with N—ClO$_3$, N—NO$_2$ or N—SO$_2$R. According to the teaching from WO 01/14401 such substances can be prepared by reacting the free hydroxyl group of a deoxy nucleoside with amidophosphonyl chloride in the presence of pyridine. However, this type of preparation is complicated, time-consuming and unsuitable for the routine synthesis of nucleotides or oligonucleotides.

The preparation of Acc azides such as acyl azides and sulfonyl azides is simple and known for a long time (Review. Brüse, S., et al., Angewandte Chemie 117 (2005) 5320-5374, 3.4 and 3.5.2). They are preferably prepared from acyl chlorides or sulfonyl chlorides using sodium azides or from hydrazides using nitrous acid.

Dye sulfonyl azides are for example also used in dyeing processes (e.g. DE 19650252). Cyanogen azide can be simply produced by reacting sodium azide with bromocyanogen in acetonitrile (McMurry, J. E. et al., J. Organic Chemistry 38(16) (1973) 2821-7). Heteroaryl azides can be prepared by nucleophilic substitution of a halogen with azide or from heteroaryl hydrazines. A prerequisite is that the electron-attracting nitrogen is in the para or ortho position relative to the azido group since only then is a resonance-stabilized phosphate mimetic formed. Ortho and para N-alkyl pyridinium azides are particularly suitable in this connection. Some acyl, sulfonyl and pyridyl azides are also commercially available.

The technical object forming the basis of the present invention was thus to provide improved labeled oligonucleotides and to provide labeling reagents which can be used within a simple process for their preparation.

SUMMARY OF THE INVENTION

Thus, the present invention is directed to a reagent having the chemical structure

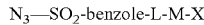

$N_3$—$SO_2$-benzole-L-M-X characterized in that L is a linker which is preferably either —NH—CO-polyethylene glycol or —NH—CO—$(CH_2)n$ with n being a natural number between 1 and 18. M is selected from a group consisting of —NH—, —O—, and —S—, and X is either a protecting group or a detectable unit. In one embodiment, X is selected from a group consisting Of DMT, TFA, Fmoc and S-alky, wherein alky is a chain of 1-6 carbon atoms. Alternatively, X is a labeling compound such as a fluorescent compound.

In a second aspect, the present invention is directed to the use of a compound with X as a protecting group as disclosed above for modifying a nucleic acid which is preferably a single stranded oligonucleotide. In a preferred embodiment, such a modification comprises steps of reacting a 3' phosphoramidite with the 5' OH end of a nascent oligonucleotide chain, and reacting the intermediate with a reagent as disclosed above.

In a third aspect, the present invention is directed to a method for preparing a reagent as disclosed above, characterized in that a compound having the chemical formula $N_3$—$SO_2$-benzole-$NH_2$ is reacted with an activated carbonic acid having the formula A-CO-L-M-X wherein L is a linker which is preferably either —$(CH_2)n$- with n being a natural number between 1 and 18 or polyethylenglycol, M is selected from a group consisting of —NH—, —O—, and —S—, X is either a protecting group or a detectable unit; and A is selected from a group consisting of chloride, anhydride, and N-hydroxysuccinimide.

Alternatively, such a reagent may be synthesized according to the invention by means of reacting a compound having the chemical formula $N_3$—$SO_2$-benzole —$(CH_2)$n-COCl with n=0-6 with a compound having the formula $NH_2$—$(CH_2)$m-M-X characterized in that m is 0 of a natural number between 1 and 10, M is selected from a group consisting of —NH—, —O—, —S—, and X is either a protecting group or a detectable unit.

DETAILED DESCRIPTION OF THE INVENTION

The object of the present invention is to provide labeling reagents which can be used to produce oligonucleotides in a simple manner which contain modified phosphate residues and thus can also preferably detectable labels.

The central idea of the present invention was to start with a bivalent phosphorus atom and to react it with a reagent in such a manner that a stable phosphate mimetic is formed. According to the invention a phosphorus atom containing at least one hydroxyl residue which is provided with a protective group is for this purpose reacted with an azide having the structure N=N=N-Acc in which Acc is an electron acceptor or an electron acceptor substituted with a residue R and R is any organic substituent. This results in the formation of a pentavalent phosphorus atom to which a strongly electron-attracting electron acceptor group is covalently bound via an N atom. This group ensures that the compounds produced in this manner are, in contrast to the phosphoramidate compounds known from the prior art, resonance-stabilized and are not susceptible to hydrolysis.

This idea underlying the invention can be applied to all processes in which a trivalent phosphorus is formed as an intermediate.

During conventional oligonucleotide synthesis using phosphoramidites, phosphonic acid triesters with a trivalent phosphorus atom are formed as intermediate products. The first and second ester bond represent the internucleoside linkage. The phosphorus atom is linked to a protected hydroxyl group such as for example to a beta-cyanoethyloxy group via the third ester bond. Instead of an oxidation with iodine, the nascent oligonucleotide can then be reacted according to the invention with an appropriate azide in the process of which the trivalent phosphorus atom is oxidized to a pentavalent atom by covalently linking —N-Acc to the phosphorus atom while cleaving nitrogen.

Oligonucleotide synthesis can then be subsequently continued as known from the prior art. Stable oligonucleotides are obtained as an end product which are modified in almost any manner on one or more internucleotide phosphate residues.

Within the scope of the present invention some of the terms used are defined as follows:

Reactive group refers to groups of a molecule which are able to react under suitable conditions with another molecule while forming a covalent bond. Examples of reactive-groups are hydroxyl groups, amino groups, thiol, hydrazino, hydroxylamino, diene, alkine and carboxylic acid groups.

Protective group denotes molecules which react with one or more reactive groups of a molecule such that, as part of a multistep synthesis reaction, only one particular, non-protected reactive group can react with the desired reaction partner. Examples of frequently used protective groups, to protect hydroxyl groups are beta-cyano-ethyl, beta-cyanomethyl, trialkylsilyl and allyl. Protective groups for protecting amino groups are trifluoroacetyl and Fmoc. Other possible protective groups are summarized in standard text books (Greene, T. W., Protective groups in organic synthesis, Wiley Interscience Publications, John Wiley & Sons (1981) New York, Chichester, Brisbane, Toronto; Souveaux, E., Methods in Mol. Biology 26 (1994) Protocols for Oligonucleotide Conjugates, Humana Press, Totowa, N.J., Chapter 1, ed. S. Agrawal).

Linkers are defined as carbon chains having a length of 0-40 C atoms. Such linker chains can also additionally have one or more internal nitrogen, oxygen, sulphur and/or phosphorus atoms. Linkers can also be branched, e.g., also, be dendritic. Linker interconnects nucleotide or a chain of nucleotides with either a detectable unit or a reactive group which is optionally protected by a protective group.

In the context of the present invention, a linker has preferably at least 6 atoms. Also preferably, the chain is composed of C atoms, which may contain up to 20 heteroatoms. In particular embodiments, such a linker my comprise one or more of the following structures: —NR—(C=O)—, —C(=O)—NR—, and —S(=O)$_2$—NR—, —NR—S(=O)$_2$— with R=H or $C_1$-$C_6$ alkyl or O—$CH_2$ $CH_2$—O.

A detectable unit is understood to denote substances which can be detected with the aid of analytical methods. They can for example be units that can be detected by mass spectroscopy, immunologically or with the aid of NMR. Detectable units are in particular also substances that can be detected by optical methods such as fluorescence and UV/VIS spectroscopy such as fluoresceins, rhodamines and gold particles. They also include intercalators and minor groove binders which can also have an effect on the melting behaviour and whose fluorescence is changed by hybridization.

Phosphoramidites denote molecules containing a divalent phosphorus atom which can be coupled to the 5' terminal end of a nucleoside or nucleoside derivative. Thus phosphoramidites can be used in oligonucleotide synthesis. In addition to (deoxy)ribonucleotide phosphoramidites that are used for chain extension, there are also phosphoramidites derivatized with a label which can be used in similar processes during or at the end of oligonucleotide synthesis to label the oligonucleotide (Reaucage, S. L., Methods in Molecular Biology 20 (1993) 33-61, ed. S. Agrawal; Wojczewski, C., et al., Synlett 10 (1999) 1667-1678).

In connection with the present invention the term "oligonucleotides" encompasses not only (deoxy) oligoribonucleotides but also oligonucleotides which contain one or more nucleotide analogues with modifications on the phosphate backbone (such as for example methyl phosphonates, phosphothioates), on the sugar (such as 2'—O-alkyl derivatives, 3' and/or 5' aminoribose; LNA, HNA, TCA) or modified bases such as 7-deazapurine. In this connection the invention also encompasses conjugates and chimeras containing non-nucleosidic analogues such as PNAs or other biopolymers, e.g., peptides. Furthermore, the oligonucleotides according to the invention can also contain one or more non-nucleosidic units such as spacers at each position, e.g., hexaethylene glycol or Cn (n=3.6) spacers.

The term "electron acceptor" encompasses atomic structures which have the tendency to attract free electron pairs. One measure of this is the Hammett constant. The present invention concerns in particular embodiments in which the Hammett constant $o_p$ exceeds a certain value of 0.30, preferably 0.45 and particularly preferably 0.60.

The electron acceptor must additionally be compatible with all chemical reactions in oligonucleotide synthesis, i.e., it should not be oxidized by iodine, it must be inert towards dichloroacetic acid and trichloroacetic acid, it must be inert towards bases and in particular towards ammonia, and it should not react with trivalent phosphoramidates. Examples of electron acceptors which fulfil these conditions are —$NO_2$, $SO_2$—R, —CN, —CO—R, pyrinidinyl, pyridinyl, pyridazinyl, hexafluorophenyl, benzotriazolyl (Hansen, C, et al., Chem. Reviews 91 (1991) 165-195). In addition these acceptors can also be bound to the nitrogen atom in a vinylogous or phenylogous manner.

The term "substituted" means that the structure that is referred to as being substituted contains another residue at any position provided this position is not defined in more detail. The term "optionally substituted" denotes that the structure referred to in this manner comprises embodiments with and without an additional residue.

The term "amino-substituted alkyl" encompasses $C_1$-$C_{30}$ linear or branched alkyl which contains at least one amino group where this amino group is protected or is bound to a detectable unit via a linker.

The term "electron-deficient, six-membered N-heterocycle" encompasses N-heterocycles which are alkylated on an sp2 nitrogen such that the overall charge of the heterocycle is positive. Examples of this are pyridinium, pyrimidinium and quinolinium.

The term "nucleotide chain" is understood as a molecule or a part of a molecule containing at least two nucleoside residues which are 5'-3' inter-connected by a phosphate moiety.

The present invention is directed to a reagent having the chemical structure $N_3$—$SO_2$-benzole-L-M-X characterized in that L is a linker structure as defined above. In one embodiment, L is preferably either —NH—CO-polyethylene glycol or —NH—CO—$(CH_2)$n with n being a natural number between 1 and 18. In another specific embodiment, L is —CO—NH-polyethylene glycol or —NH—CO—$(CH_2)$n with n being a natural number between 1 and 18. M is selected from a group consisting of —NH—, —O—, and —S—, and X is either a protecting group or a detectable unit.

The moieties linked to the benzole are positioned either in meta configuration or in a para configuration. Preferably they are in a para configuration. In addition, the benzole may be substituted at one or more positions by non bulky substituents like halogens such as chloride.

In case L is —$(CH_2)$n- n is a natural number between 1 and 18, preferably between 2 and 12 and most preferably between 3, and 6.

In case L is a polyethylene glycol, the chain length may preferably vary between 2 (diethylenglycol) and 6 (hexaethylenglycol).

Preferably, M is —NH—.

In case X is a protecting group, it is selected from a group consisting of DMT (dimethoxytrityl), TFA (trifluoracetyl), Fmoc ((fluoren-9-yl)methoxy-carbonyl), -and —S-alkyl, wherein said alkyl group has a chain length of 1-6 carbon atoms. Depending on the nature of M, different protecting groups are selected. For —NH—, TFA and Fmoc are highly preferred. For —O—and —S', it is advisable to use DMT. For —S—, —S-alkyl may be used.

In case X is a detectable unit; said detectable unit may be a color label dye such as a fluorescent label. Further examples are mass tags, haptens like digoxygenin or biotin, or small peptides, all of which are detectable by an antibody. Preferably, X is a fluorescent compound such as for example fluorescein or any other fluorescent dye which is used in real time PCR.

If is noted that the definitions and disclosed specific embodiments of X, M, and L also apply to the following chapters disclosing "synthesis of chemical labeling reagents according to the present invention", "production of oligonucleotides according to the invention", and "oligonucleotides generated with a labeling reagent according to the present invention".

The present invention also provides an easy and straight forward method for synthesizing a compound according to the present invention.

A compound having the chemical formula $N_3$—$SO_2$-benzole-$NH_2$ is easily available by standard methods known in the art from reasonable cheap commercially available $N_3$—$SO_2$-benzole-NH acetyl.

This chemical compound is reacted with an activated carbonic acid having the formula A-CO—I-M-X characterized in that A is selected from a group consisting of chloride, anhydride and N-hydroxysuccinimide (NHS ester). Preferably, A is N-hydroxysuccinimide.

L is a linker which is preferably either —$(CH_2)$n- or polyethylene glycol. In case L is —$(CH_2)$n-, is a natural number between 1 and 18, preferably between 2 and 12 and most preferably between 3 and 6. In case L is a polyethylene glycol, the chain length may preferably vary between 2 (diethylenglycol) and 6 (hexaethylenglycol). M is selected from a group consisting of —NH—, —O—, and —S—, and X is either a protecting group or a detectable unit as disclosed above.

Some compounds which are covered by the general structure A-O—CO-L-M-X are also commercially available as reagents which are offered for post snthesis labeling of oligonucleotides. In particular, fluorescent dyes are frequently offered in the form of NHS esters as it is the case for LC Red 640 and LC Red 610 (Roche Applied Science Cat. Nos: 12 015 161 001, 03, 03 561 488 001). In the context of the present invention, however, such compounds are reacted first with $N_3$—$SO_2$-benzole-$NH_2$ with the result that such compounds are then available in the form of an azide. As described below such azides subsequently may be used for introducing a label already during oligonucleotide synthesis.

Alternatively, synthesis of a labeling reagent can be performed by synthesing $N_3$—$SO_2$-benzole-L-NH—X with X as a protective group according to the method described above and then deprotecting X, whereas X has to be chosen from a protective groups which can be removed under conditions where the azid is reasonable stable. Suitable protective groups are Trityl, Boc, and Phenylacetyl. The resulting $N_3$—$SO_2$-benzole-L-$NH_2$ can then be reacted with activated esters of detectable group, for example with commercially available NHS esters of dyes.

In another aspect of the invention the synthesis can be started from compounds $N_3$—$SO_2$-benzole-(L)n-C(=O)Cl with n=0-1. Such compounds are easily synthesized from Arylsulfonylchorides which are substituted with a carboxylic acid whereas the carboxylic acid can be directly attached to the Aryl ring or via a linking moiety. Commerically available compounds are eg Cl—S(=O)2-Ph-COOH or Cl—S(=O)2-Ph-(CH2)2COOH. The Sulfonylchloride is transferred to the Sulfonylazide by reacting with Sodium azide and then the carboxylic acid can be converted to the acid chloride by standard methods (e.g., FR 1455154). Alternatively, N3—S(=O)2-Ph-NH2 can be reacted with a dicarboxylic acid anhydride to N3—S(=O)2-Ph-NH C(=O) (CH2) COOH, followed by conversion of the carboxylic acid to the acid chloride by standard methods. Compounds $N_3$—$SO_2$-benzole-(L)n-C(=O)Cl can then be reacted with NH2-L-M-X, which is commercially available or can be easily synthesized from NHS esters of detectable groups by reacting said esters with an excess of $NH_2$-L-$NH_2$.

In general the present invention concerns labeling reagents for producing modified oligonucleotides which are characterized in that a trivalent phosphorus derivative of the chemical structure

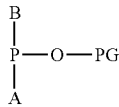

in which PG represents a protective group, A represents the 5' end of a nucleotide or of a nucleotide chain or it represents a linker bound to a solid phase, and B presents the 3' end of a nucleotide or of a nucleotide chain or it represents a linker, is reacted with an azide of the structure $N_3$—$SO_2$-benzole-L-M-X, characterized in that L is a linker which is preferably either —NH—CO-polyethylene glycol or —NH—CO—(CH$_2$)n with n being a natural number between 1 and 18, M is selected from a group consisting of —NH—, —O—, and —S—, and X is either a protecting group or a detectable unit.

Beta-cyanoethyl, methyl, allyl or silyl are particularly preferred as protective groups (PG). Alternatively methyl-phosphonates can be produced according to the invention in which —O-PG is replaced by $CH_3$.

The process according to the invention can also be routinely used in particular within a conventional oligonucleotide synthesis. Hence the present invention also concerns a process comprising the steps a) reaction of a 3' phosphoramidite with the 5' OH end of a nascent oligonucleotide chain and b) reaction with an azide of the structure $N_3$—$SO_2$-benzole-L-M X, characterized in that L is a linker which is preferably either —NH—CO-polyethylene glycol or —NH—CO—(CH$_2$)n with n being a natural number between 1 and 18. M is selected from a group consisting of —NH—, —O—, and —S—, and X is either a protecting group or a detectable unit.

In this case the 5' OH end of the nascent oligonucleotide chain can either be the 5' end of a 5' terminal nucleotide or the free OH group of a CPG.

Conventional oligonucleotide chemistry begins on a reactive solid phase support material. Solid phase support material refers to polymeric substances which form a solid phase containing a reactive group on which further molecules can be immobilized. In the case of oligonucleotide synthesis, the support material is usually porous glass beads with a defined pore size, so-called controlled pore glass particles (CPG). Alternatively it is also possible to use polystyrene residues and other organic polymers and copolymers (Ghosh, P. K., et al., J. Indian. Chem. Soc. 75 (1998) 206-218). If the oligonucleotides should remain immobilized after the synthesis on the substrate, glass and also semiconductor chips can be used as the solid phase support material. Such solid phase support materials are commercially available.

The support can be bound by means of a so-called linker group containing a cleavable bond to the terminal reactive hydroxyl residue protected by a protective group such as DMT (dimethoxytrityl). A linker group with a cleavable bond denotes those groups which are between the trifunctional spacer and the solid phase support material and can be cleaved by a simple chemical reaction. They can be succinyl or oxalyl or other linker groups which contain a cleavable ester bond. Other linker groups are known to a person skilled in the art (Ghosh, P. K., et al., J. Indian. Chem. Soc. 75 (1998) 206-218).

Such linker groups are essential for the use of the support material to synthesize oligonucleotides which are intended to be present in aqueous solution after completion of the synthesis. If, in contrast, the oligonucleotide should remain on the surface of the support material after the synthesis as for the production of nucleic acid arrays (U.S. Pat. No. 5,624,711; Shchepinov, M. S., el al., NuCl. Acids. Res. 25 (1997) 1155-1161), a cleavable linker groups is unnecessary but rather a non-cleavable linker group is preferred.

The details of an oligonucleotide synthesis for the incorporation of the structures according to the invention are as follows:

A reactive hydroxyl group on which a chain extension in the 3'→5' direction can occur is formed after removing the DMT protective group by acid treatment. Then 3' phosphoramidite derivatives of (deoxy) ribonucleosides that are also provided with a DMT protective group are successively coupled at the 5' end to each reactive group freed of the DMT protective group in the presence of tetrazole. An intermediate containing a trivalent phosphorus atom is formed in this process as an intermediate product which forms an ester bond with each of the nucleosides that are linked together by the reaction and a third ester bond with a protected hydroxyl group which is already present in the phosphoramidite is used. This protective group which can for example be formed by beta-cyanoethyl, methyl, allyl or silyl is subsequently cleaved with ammonia after completion of the oligonucleotide synthesis in the process of which the base protective groups and the linker to the CPG are also cleaved.

Instead of oxidation with the aid of iodine, the nascent oligonucleotide is reacted according to the invention with an azide of the structure N₃—SO₂-benzole-L-M-X, characterized in that L is a linker which is preferably either —NH—CO-polyethylene glycol or —NH—CO—(CH₂)n with n being a natural number between, 1 and 18. M is selected from a group consisting of —NH—, —O—, and —S—, and X is either a protecting group or a detectable unit at the positions at which phosphate mimetics are to be introduced into the nucleotide chain.

In particular, if X is protecting group, X can be removed after oligonucleotide and a post oligonucleotide synthesis labeling with a reactive detectable unit can be performed as it is well known in the art.

Preferably, however, X is a detectable unit, for example a fluorescent molecule and thus, labeling of the nascent oligonucleotide is taking place already during the phosphoramidite based oligonucleotide synthesis.

Certain embodiments of the present invention concern the preparation of dual labeled oligonucleotide probes in which a label is preferably introduced internally into the oligonucleotide according to the inventive process and another label is introduced into the oligonucleotide preferably at the 5' or 3' end according to a method known from the prior art.

In the case of a 5' label at the 5' position of the ribose of the 5'-terminal nucleotide, the incorporation is carried out by conventional methods using a dye-labeled phosphoramidite at the end of the oligonucleotide synthesis (Beaucage, S. L., Methods in Molecular Biology 20 (1993) 33-61, S. Agrawal Publishers).

Labeling at the 3' end is carried out by using commercially available CPG as a reactive solid phase support which already contains a detectable label in addition to the tritylated hydroxyl group. After cleavage of the DMT protective group standard oligonucleotide synthesis can be started at the hydroxyl group which is now free.

Alternatively methods known from the prior art for post-labeling can be used for an additional 5' or 3' label (U.S. Pat. Nos. 5,002,885; 5,401,837).

The invention also concerns intermediates of the synthesis according to the invention which can be prepared before the standard oligonucleotide synthesis. In this case intermediates that are still bound to the solid phase and are not yet deprotected and can contain a basic spacer groups are preferred. CPGs which are familiar to a person skilled in the art as phosphate CPG are preferably used for the preparation since a 3' phosphorylated oligonucleotide is formed after the oligosynthesis. After detritylation such phosphate CPGs are reacted with a spacer phosphoramidite in the presence of an activator. The trivalent phosphorus intermediate that is formed is then reacted with an N₃—SO₂-benzole-L-M-X as disclosed above where X is a detectable unit. These intermediates of synthesis can be stored and used like trifunctional CPGs for universal 3' labeling.

A trivalent phosphorus intermediate is also formed during the synthesis of methyl phosphonates which can be reacted with an azid according to the present invention. Methyl phosphoramidites are also commercially available.

In an inverse synthesis strategy (EP 1 155 027) which is used for standard oligonucleotides as well as in particular for analogues, e.g., for the synthesis of N3'→P5' oligonucleotides, an intermediate containing a trivalent phosphorus is also formed which can be reacted according to the invention with an azid according to the invention. The corresponding phosphoramidites are commercially available.

Oligonucleotides Generated with a Labeling Reagent According to the Present Invention The synthesis strategy according to the invention allows the preparation of a wide variety of oligonucleotides modified on the phosphate backbone. The degree of modification, the diversity and the charge of the modifications are determined by the intended use.

The present invention encompasses any chemical compound containing the following structure at least once

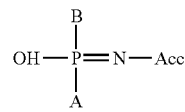

in which A represents the 5' end of a nucleotide or of a nucleotide chain or OH, B represents the 3' end of a nucleotide or of a nucleotide chain or OH, and Acc represents —SO₂-benzole-L-M-X, characterized in that L is a linker which is preferably either —NH—CO-polyethylene glycol or —NH—CO—(CH₂)n with n being a natural number between 1 and 18. M is selected from a group consisting of —NH—, —O—, and —S—, and X is either a protecting group or a detectable unit. It is also understood by a person skilled in the art that the —OH groups of the oligonucleotide are usually present in a deprotonated status.

Moreover the present invention also encompasses methyl phosphonates of the following structure

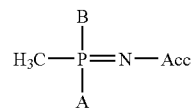

Depending on the intended use of the oligonucleotide, the structures described above can occur once, twice, many times or even on all phosphate residues present in the oligonucleotide. The phosphate residues within the oligonucleotide are so-called internucleoside phosphates in which A represents the 5' end of a first nucleoside and B represents the 3' end of a second nucleoside within the nucleotide/chain.

Furthermore the structures according to the invention can be located at the 3' end or 5' end of an oligonucleotide. If they are present at the 5' end of the oligonucleotide, then A represents the 5' end of the nucleotide chain and B is either a hydroxyl group or a linker which can optionally contain a detectable group or another reactive group, and can be used to synthesize a detectable group on the oligonucleotide.

If the electron acceptor contains a substituent which also represents a detectable unit, then an oligonucleotide is present according to the invention with a dual label at the 5' end. If the structure according to the invention is at the 3' end of a nucleotide chain, then B represents the 3' end of the said oligonucleotide and A is either hydroxyl or a linker bound to a solid phase wherein the solid phase is preferably controlled pore glass particles such as those that are used as a starting material for routine oligonucleotide synthesis.

The individual nucleosides within the oligonucleotides according to the invention can contain any type of nucleosides or modified nucleosides or nucleoside derivatives. The sugar units are usually deoxyribose for DNA oligonucleotides or ribose for RNA oligonucleotides. The nucleobases contained in the oligonucleotides according to the invention can be naturally occurring bases such as adenine, guanine, thymidine, cytidine, uridine, derivatives thereof of so-called universal bases such as nitroindole.

Oligonucleotides labeled with a labeling reagent according to the present invention can be used advantageously for numerous different applications in molecular biology such as in real time PCR. The detectable label is preferably a fluorescent dye or a fluorescence quencher molecule. Corresponding dyes and molecules which can serve as a detectable unit for oligonucleotides are well known to a person skilled in the art. Examples of these that do not limit the protective scope of the present invention are: fluoresceins, rhodamines, cyanines, merocyanines, carbocyanines and azo and poly-azo compounds.

The labeling reagent according to the present invention may be used to synthesize real time PCR probes having the structure described above in which at least one fluorescent label is bound to the phosphate atom of the oligonucleotide chain by means of an amide/electron acceptor group. Examples of such probes are FRET hybridization probes (WO 97/46707) or so-called single-labeled probes (WO 02/14555). In this connection oligonucleotide probes in which there is an internal modification according to the invention on an internucleoside phosphate, residue are particularly preferred.

In this connection the labeling reagent according to the present invention present is particularly usefull to produce dual labeled oligonucleotides which have two detectable units. Examples of such probes are TaqMan probes (U.S. Pat. No. 5,804,375) molecular beacons (U.S. Pat. No. 5,118,801). In this connection the present invention concerns preparation of dual labeled oligonucleotides in which a first fluorescent label is bound to an internucleoside phosphate atom of the oligonucleotide chain by means of an amide/electron acceptor group and a second detectable unit is present terminally at the 5' end or 3' end of the oligonucleotide. Molecules which have such labels and methods for their preparation are well-known among experts.

The invention is elucidated in more detail by the following examples, the protective scope of which is derived from the patent claims. The described methods are to be understood as examples which still describe the object of the invention even after modifications.

The following examples are provided to aid the understanding of the present invention, the true scope of which is set forth in the appended claims. It is understood that modifications can be made in the procedures set forth without departing from the spirit of the invention.

EXAMPLE 1

4-Aminobenzenesulfonyl Azide (According DE 2919823)

2.0 g (8 mmol) p-Acetylaminobenzoylsulfonylazide was stirred with 4.0 g (3.4 mL) of 32% hydrogen chloride and heated up to 95° C. in 20 min. A clear solution was formed. Upon cooling to room temperature, the hydrochloride precipitates and was separated by filtration. The crystals were dissolved in 20 ml water and a saturated sodium carbonate solution was added and the aqeuous phase was then extracted 3 times with dichlormethane. The combined organic phases were washed with water and dried with sodium sulphate. After removing the solvents the resulting pale red oil was dried overnight on calcium chloride under vacuum to yield 1.04 g (66%) crude product.

TLC Silica on Plastic Sheet (toluene:ethylacetate:methanol=4:1:1) Rt(Product)=0.63,

EXAMPLE 2

(2,2,2-trifluoro-acetylamino)-hexanoyl chloride 735 mg(3 mmol) (2,2,2-trifluoro-acetylamino)-hexanoic acid were dissolved in 5 mL dried dichloromethane and stirred under argon flux at 0° C. Then, 0.6 mL (6.6 mmol) oxalyl chloride were added dropwise at 0° C., a few drops of dried dimethylformamide were also added dropwise which lead to gas development and yellow colouring of the previously white mixture. The mixture, was stirred at room temperature for 70 min. Then the mixture was repeatedly evaporated with dichloromethane. The crude product was used directly in the next step.

EXAMPLE 3

4-[6-(2,2,2-Trifluoro-acetylamino)-hexanoylamino]-benzenesulfonyl azide

To 0.57 g (3 mmol) of para-amino-benzenesulfonyl azide dissolved in 5 mL dimethylformamide was added 0.9 mL (6 mmol) triethylamine, then the (2,2,2-trifluro-acetylamino)-hexanoyl chloride dissolved in 10 mL dimethylformamide was added dropwise. The mixture turned brown and was stirred under argon for 24 hrs. Solvent was evaporated, and the remaining oil was dissolved in 10 mL dichloromethane and left at room temperature for 1 hr. The precipitate was filtrated and the solution was evaporated to yield 1.10 g crude oil. The obtained compound was directly used in oligonucleotide synthesis.

EXAMPLE 4

Synthesis of an Amino-Modified Oligonucleotide

```
                                          (SEQ ID NO: 1)
5' Ap*GG GAT CTG CTC TTA CAG ATT AGA AGT AGT CCT
ATT-p
p* = p = N-SO2-Ph-NH-C(=O)-(CH2)5-NH2
```

The oligonucleotide synthesis was carried out on a 1 μmol scale on an ABI 394 synthesizer. Commercially available Phosphate CPG (Glen Research) was used as the support material. All other chemicals for the standard synthesis-were obtained from Glen Research. Phosphoramidites with tert butylphenoxy-acetyl protective groups (known as "tac" or "Expedite" monomers) from Proligo were used.

The standard protocol was used for the synthesis. Only in the last synthesis cycle, the oxidizer was replaced by a 0.1 M solution of 4-[6-(2,2,2-trifluoro-acetylamino)-hexanoylamino]-benzenesulfonyl azide in anhydrous acetonitrile and the "oxidation" time was extended to 16 min.

The product was cleaved from the support for 15 h at 55° C. with 33% ammonia and purified by reversed phase chromatography on a Poros Oligo R3 4.6×50 mm column. Chromatography: buffer A: 0.1 M triethylammonium acetate in water pH 6.8, buffer B: 0.1 M triethylammonium acetate in water/acetonitrile 1:1, gradient 2 min 0% B to 100% B in 45 min. The UV absorption of the eluant was measured at 260 nm. A main fraction was obtained which contained the aminomodified oligonucleotide. The solvent was removed on a vacuum centrifuge.

EXAMPLE 5

Postlabeling with LIGHTCYCLER Red 640

```
                                              (SEQ ID NO: 2)
5' Ap*GG GAT CTG CTC TTA CAG ATT AGA AGT AGT CCT
ATT-p
p* = p = N-SO2-Ph-NH-C(=O)-(CH2)5-NH LC Red 640
```

The residue was taken up in 1 ml 6.1 M sodium borate buffer (pH=8.5). A solution of 1 mg LIGHTCYCLER (Roche Diagnostics GmbH) Red 640 NHS ester (Roche Applied Science) in 1000 µl DMF was added and the mixture was kept at room temperature Overnight. The mixture was evaporated in and purified under the same conditions as described above. As detector, a diode array was used an detection was performed at 260 and 625 nm. Fractions having both absorptions were collected and evaporated in vaccuum. The remainder was dissolved in bidest. water and again evaporated in vacuum. The residue was then dissolved in bidest. water and lyophilized.

MALDI: calc: 12438.35 Found: 12435.5

EXAMPLE 6

N-Dansyl 3 Amino Propanoyl Chloride 970 mg(3 mmol) dansyl beta alanin were dissolved in 5 mL dried dichloromethane and stirred under argon flux at 0° C. Then 0.6 mL (6.6 mmol) oxalyl chloride was added drop wise at 0° C., and subsequently, a few drops of dried dimethylformamide were added which lead to gas development. The mixture was stirred at room temperature for 100 min. The solvents were removed by using a rotary evaporator and then the remainder was twice evaporated with dichloromethane. The crude product was used directly in the next step.

EXAMPLE 7

N-Dansyl (3 aminopropanoyl) benzenesulfonyl azid

To 152 mg (0.8 mmol) of para-amino-benzenesulfonyl azide dissolved in 5 mL dimethylformamide was added 0.11 mL (6 mmol) triethylamine, then 0.5 mmol N-Dansyl 3 aminopropanoyl chloride dissolved in 10 mL dimethylformamide was added dropwise. The mixture was stirred under argon for 24 hrs. The solvent was evaporated, the remaining oil was purified by chromatography on silica (Eluent Toluol/Aceticacidethylester 1:1). The fractions containing the product were collected and the solution was evaporated.

1H NMR (Bruker DPX 300 MHz): d6 DMSO: 2.53 m [2H], 2.82 s[6H], 3.12 m [2H], 7.20 m [2H], 7.59 t [1H], 7.62 t [1H], 7.81 d[2H], 7.93 d[2H], 8.07 t [1H], 8.12 d [1H], 8.27 d[1H], 8.44[1H], 10.47 s [1H], (protonated form) IR (Nujol) 2122 cm-1

MALDI: calc: 11436.7 found 11435.6

What is claimed is:

1. A reagent having the structure $$N_3\text{-}SO_2\text{-benzole-}L\text{-}M\text{-}X$$

wherein L is —NH—CO-polyethylene glycol or —NH—CO—(CH2)n wherein n is a natural number between 1 and 18, M is —NH—, —O—, or —S—, and X is a protecting group or a detectable unit.

2. The reagent of claim 1 wherein X is a protecting group selected from the group consisting of dimethoxytrityl (DMT), trifluoracetyl (TFA), (fluoren-9-yl)methoxy-carbonyl (Fmoc); and S—$C_{1-6}$-alkyl.

3. The reagent of claim 1 wherein X is a detectable unit selected from the group consisting of fluorescent compounds, gold particles, digoxigenin, and biotin.

4. A method for modifying a single stranded oligonucleotide comprising the steps of reacting a 3' phosphoramidite with a 5' OH end of a nascent oligonucleotide chain and then reacting the 3' phosphoramidite with a reagent having a structure $$N_3\text{-}SO_2\text{-benzole-}L\text{-}M\text{-}X$$

wherein L is —NH—CO-polyethylene glycol or —NH—CO—(CH2)n wherein n is a natural number between 1 and 18, M is —NH—, —O—, or —S—, and X is a protecting group or a detectable unit, under conditions whereby said single stranded oligonucleotide is modified.

5. A method for preparing a reagent according to claim 1 comprising the step of
reacting a compound having the formula $N_3$—$SO_2$-benzole-$NH_2$ with an activated carbonic acid having the formula A-CO-L-M-X wherein L is —(CH$_2$)n- or polyethylene glycol, M is selected from the group consisting of —NH—, —O—, and —S—, X is either a protecting group or a detectable unit, and A is selected from the group consisting of chloride, anhydride, and N-hydroxysuccinimide, under conditions whereby said reagent is formed.

6. A method for preparing a reagent according to claim 1 comprising the step of
reacting a compound having the formula $N_3$—$SO_2$-benzole-(CH$_2$)n-COCl wherein n is 0 or a natural number between 1 and 10 with a compound having the formula $NH_2$—(CH$_2$)m-M-X wherein m is 0 or a natural number between 1 and 10, M is selected from the group consisting of —NH—, —O—, and —S—, and X is a protecting group or a detectable unit, under conditions whereby said reagent is formed.

* * * * *